United States Patent [19]

Lee et al.

[11] Patent Number: 4,661,645

[45] Date of Patent: Apr. 28, 1987

[54] SYNTHESIS OF STYRENATED HYDROQUINONE

[75] Inventors: David M. Lee; David A. Hutchings, both of Newark; Gloria M. Sieloff, Pataskala; G. Fred Willard, Newark, all of Ohio

[73] Assignee: Owens-Corning Fiberglas Corporation, Toledo, Ohio

[21] Appl. No.: 836,902

[22] Filed: Mar. 6, 1986

Related U.S. Application Data

[63] Continuation-in-part of Ser. No. 655,803, Oct. 1, 1984, abandoned.

[51] Int. Cl.$^4$ .............................................. C07C 39/14
[52] U.S. Cl. ....................................... 568/744; 568/780
[58] Field of Search ................................ 568/744, 780

[56] References Cited

U.S. PATENT DOCUMENTS 2,432,356 12/1947 Underwood ......................... 568/744
2,506,410 5/1950 Blake ................................... 568/744
3,772,393 11/1973 Hunter ................................ 568/744

Primary Examiner—Warren B. Lone
Attorney, Agent, or Firm—Ronald C. Hudgens; Robert F. Rywalski

[57] ABSTRACT

Styrene and hydroquinone are reacted to produce (1-phenylethyl) hydroquinone, i.e.,

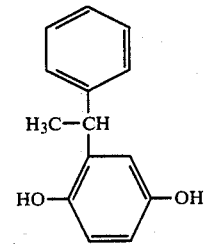

15 Claims, No Drawings

SYNTHESIS OF STYRENATED HYDROQUINONE

CROSS REFERENCES

The present application is a continuation-in-part of application of U.S. Ser. No. 655,803, filed Oct. 1, 1984, now abandoned, which application is also hereby incorporated by reference.

The present invention is related to copending application U.S. Ser. No. 581,166 entitled MELT PROCESSABLE OPTICALLY ANISOTROPIC POLYMERS which application is hereby incorporated by reference. This application is also related to copending application U.S. Ser. No. 819,945 which is likewise hereby incorporated by reference.

TECHNICAL FIELD

The present invention relates to substituted hydroquinone compounds and, more particularly, it relates to the synthesis of (1-phenylethyl) hydroquinone.

BACKGROUND AND SUMMARY

In accordance with the present invention, (1-phenylethyl) hydroquinone is synthesized by reacting styrene with hydroquinone in the presence of an organic diluent and in the presence of effective reaction stimulating amounts of a Lewis acid. The crude (1-phenylethyl) hydroquinone reaction product and unreacted reactants are then vacuum distilled to obtain a fraction consisting primarily of the (1-phenylethyl) hydroquinone. The vacuum distillation is done in the presence of an organic diluent which co-distills with unreacted hydroquinone under the conditions of vacuum distillation. Exemplary of suitable Lewis acids are: para-toluene sulfonic acid, sulfuric acid, boron trifluoride, hydrofluoric acid, stannic chloride and aluminum trichloride.

Desirably, the diluent is an ether, for example, a lower ($C_1$–$C_5$) alkyl ether including, for example, ethyl ether and tetrahydrofuran, and most desirably, a liquid polyether like the dialkoxy tetraglycols wherein the alkoxy group contains up to four carbon atoms. Other diluents include halogenated benzenes, for example, tribromobenzene, hexadecane, pentadecane and octylether. The diluent employed during the reaction (reaction diluent) will be a solvent for the reactants and the products, and as indicated above, preferably will be an ether. Desirably, the material has a boiling point in excess of about 135° C. By performing the reaction in a reaction diluent, good yields are obtained. By using a desired organic diluent during distillation (distillation diluent), a practical benefit is obtained and a problem is solved. The distillation diluent is selected to co-distill with hydroquinone so as to allow for the recovery of substantial amounts of the monosubstituted material and at the same time prevent plugging of the distillation column by the hydroquinone. The reaction is done at a suitable temperature and for a suitable time effective to form the product and preferably is conducted at approximately 135° C. to about 145° C. for several hours. The crude product is purified by high vacuum batch distillation. Generally, the organic diluent employed during distillation will have a boiling point in the range of about 270°–290° C. and it is generally preferred to use as the reaction diluent material that will function as the distillation diluent. In the preferred technique, the diluent will be tetraethyleneglycol dimethylether, that is, a material of the formula $CH_3(OCH_2CH_2)_4OCH_3$ (also known as dimethoxytetraglycol) which is commercially available under the trade designation Tetraglyme material. The preferred Lewis acid is para-toluene sulfonic acid, and, in this case, it is preferred to purify the crude (1-phenylethyl) hydroquinone product by distillation employing sodium hydrogen sulfite, or other alkali metal hydrogen sulfite, to neutralize the para-toluene sulfonic acid catalyst and prevent oxidation of hydroquinone and the synthesized (1-phenylethyl) hydroquinone to quinones.

Since an object of the present invention is to form the monosubstituted i.e., (1-phenylethyl) hydroquinone in high yields, the stoichiometry employed will generally be about an equimolar amount of hydroquinone to styrene and preferably a slight molar excess of hydroquinone to styrene. Accordingly, desirable molar ratios of hydroquinone to styrene will be about 1:1 to about 1.20:1 or even 1.25:1 if desired.

The (1-phenylethyl) hydroquinone produced in accordance with the present invention is ideally suited as a reactant for a wide variety of chemical reactions wherein the mono substituted diol is needed. It is especially useful in producing polyester resins in the manner set forth in the above incorporated U.S. patent application Ser. Nos. 581,166 and 819,945.

EXAMPLE

Into a 50 liter three-necked round-bottom flask, there is charged 5 Kg (45.4 moles) of hydroqinone (Technical Grade Hydroquinone available from Eastman Chemical Products, Inc.). Additionally, there is charged 10 liters of Tetraglyme material and 60 grams (0.32 moles) of para-toluene sulfonic acid monohydrate. A mechanical stirrer with a ground glass shaft is employed, and, while stirring slowly, the reagent mixture is warmed to about 140° C. While maintaining that temperature, 4.166 Kg (40 moles) of styrene is added over approximately a 90-minute period. During the addition of the styrene, a slight exothermic reaction sets in, and the temperature is maintained at approximately 140° C. plus or minus about 5° C. After the styrene addition is finished, the reaction mixture is held at that temperature for approximately 5 hours after which time the heating and stirring is turned off and the mixture allowed to cool overnight. The crude product has the appearance of a heavy motor oil both in relative viscosity and color, and it is homogeneous and free of suspended solids. The yield is about 19.316 Kg.

The crude product is purified by high vacuum batch distillation employing a 12 liter flask reboiler with agitator and vacuum, a 4 ft.×2" column packed with about 30" of crimped wire mesh packing, a cooled reflux condenser, a heat traced reflux splitter, receiver and associated piping. In a typical distillation, approximately 10 Kg of crude product is charged employing about 31 grams of sodium hydrogen sulfite to neutralize the para-toluene sulfonic acid catalyst. Distillation breakdown with one distillation is set forth in Table I. One redistillation of all the best fractions (fractions 4 & 5) easily yields a 96% plus pure (1-phenylethyl) hydroquinone product. The (1-phenylethyl) hydroquinone material generally may be described as a glassy material.

TABLE I

| Fraction No. | Weight Grams | (1-Phenylethyl) hydroquinone Distillation Charge Weight 10,000 grams Temperature °C. RFX/REB @ P | Composition % Styrene | % HQ/TG | % PEHQ | % DPEHQ |
| --- | --- | --- | --- | --- | --- | --- |
| 1 | 150 | 122°/162° @ 3 mm | 20 | 80 | — | — |
| 2 | 3030 | 130°/163° @ 2 mm | <2 | 95 | <2 | — |
| 3 | 2225 | 124°/189° @ .4 mm | — | 95 | <3 | — |
| 4 | 925 | 174°/212° @ 25 mm | — | 7 | 93 | — |
| 5 | 2103 | 198°/249° @ .6 mm | — | 4 | 94 | 2 |
| 6 | 142 | 205°/265° @ .7 mm | — | — | 50 | 50 |
| Residue | 1378 | — | — | — | 2 | 85 |

RFX = Reflux
REB = Reboiler
P = Pressure
HQ = Hydroquinone
TG = Tetraglyme material
PEHQ = (1-Phenylethyl)hydroquinone
DPEHQ = Di(phenylethyl)hydroquinone - probably a mixture of 2,5-DPEHQ and 2,6-DPEHQ In the above it will be noted that the distillation diluent and the reaction diluent were the same as this is generally the preferred technique for practicing the present invention. If, however, it is desired to use different diluents, obviously the reaction diluent can be removed from the reaction mixture prior to purifying the crude product. Another suitable diluent can be added and the distillation effected in the presence of this distillation diluent.

The present process provides for a high yield of the monosubstituted material i.e., (1-phenylethyl) hydroquinone relative to any di-substituted material. Generally, the ratio of monosubstituted material to di-substituted material in the crude product will be at least about 1.8:1 (weight basis) and typically in excess of about 2.3:1. In the example, calculating, for the monosubstituted material and the di-substituted material based on the data set forth in Table I, and then adjusting those values, which are based on a 10 Kg charge of crude product, for the total yield of 19.316 Kg, results in a ratio of monosubstituted material to di-substituted material of about 2.39. As previously also indicated, it is important that the organic distillation diluent co-distill with the unreacted hydroquinone under the conditions of vacuum distillation. The column "HQ/TG" in Table I, especially fractions 1, 2 and 3, and to a lesser extent, fractions 4 and 5 exemplifies this co-distillation. In addition to having what is believed to be a beneficial impact on producing a high yield of the monosubstituted material, the diluent which co-distills with the hydroquinone, solves a practical problem. Unreacted hydroquinone, because of its high melting point, will plug a conventional distillation column under these conditions of vacuum distillation but now, in the presence of the distillation diluent, this problem is substantially eliminated. In vacuum distilling the crude product, a fraction (or fraction) is obtained which is primarily, for example at least 90% by weight, monosubstituted material, i.e., (1-phenylethyl) hydroquinone. See for example, fractions 4 and 5 in Table I. Such fractions can then be expediently distilled further to obtain high purity (1-phenylethyl) hydroquinone.

While the above describes the present invention, it will, of course, be apparent that modifications are possible which, pursuant to the patent statutes and laws, do not depart in the spirit and scope thereof.

We claim:

1. A method for preparing (1-phenylethyl) hydroquinone comprising reacting styrene and hydroquinone, in the presence of an organic diluent at a temperature and for a time sufficient to form a crude product having substantial amounts of said (1-phenylethyl) hydroquinone and containing unreacted hydroquinone, vacuum distilling said crude product in the presence of said diluent to obtain a fraction consisting primarily of said (1-phenylethyl) hydroquinone, and wherein said organic diluent co-distills with said unreacted hydroquinone under the conditions of vacuum distillation.

2. The method of claim 1 wherein said fraction contains at least about 93% by weight of said (1-phenylethyl) hydroquinone.

3. The method of claim 1 wherein said fraction contains about 94% by weight of said (1-phenylethyl) hydroquinone.

4. The method of claim 1 wherein said fraction contains less than about 7% by weight of a mixture of said diluent and hydroquinone and less than 2% by weight of (di-phenylethyl) hydroquinone.

5. The method of claim 1 wherein said diluent is a dialkoxy tetraglycol wherein the alkoxy group contains up to 4 carbon atoms.

6. The method of claim 4 comprising distilling said fraction to obtain a product consisting essentially of at least about 96% pure (1-phenylethyl) hydroquinone.

7. The method of claim 5 wherein said dialkoxy tetraglycol is dimethoxytetraglycol.

8. A method for preparing (1-phenylethyl) hydroquinone comprising reacting styrene and hydroquinone in a molar ratio of hydroquinone to styrene of at least 1:1 in the presence of an organic reaction diluent at a temperature and for a time sufficient to form a crude product having a weight ratio of (1-phenylethyl) hydroquinone to di-substituted phenylethyl hydroquinone of at least about 1.8:1, said crude product also containing unreacted hydroquinone, and vacuum distilling said crude product in the presence of an organic distillation diluent to obtain a fraction comprising at least 90% by weight of (1-phenylethyl) hydroquinone, and wherein said organic distillation diluent co-distills with said unreacted hydroquinone under the conditions of vacuum distillation.

9. The method of claim 8 wherein said fraction of at least 90% by weight of (1-phenylethyl) hydroquinone is redistilled to produce at least 96% by weight pure (1-phenylethyl) hydroquinone.

10. The method of claim 8 wherein said organic reaction diluent and said organic distillation diluent are substantially the same.

11. The method of claim 10 wherein said ratio of (1-phenylethyl) hydroquinone to di-substituted (phenylethyl) hydroquinone is at least 2.3:1.

12. The method of claim 10 wherein the crude product is vacuum distilled to obtain a fraction of at least 93% by weight (1-phenylethyl) hydroquinone.

13. The method of claim 10 wherein the reaction is done in the presence of an effective reaction stimulating amount of para-toluene sulfonic acid and wherein said distillation is done in the presence of an effective para-toluene sulfonic acid neutralizing amount of sodium hydrogen sulfite.

14. The method of claim 8 wherein said organic reaction diluent is selected from the group consisting of ($C_1$–$C_5$) alkyl ethers, tetrahydrofuran, dialkoxy tetraglycols wherein the alkoxy group contains up to 4 carbon atoms, octylether, pentadecane, hexadecane, and halogenated benzenes.

15. The method of claim 14 wherein said organic distillation diluent is selected from the group consisting of dialkoxy tetraglycols wherein the alkoxy group contains up to 4 carbon atoms, octylether, pentadecane, hexadecane, and halogenated benzenes.

* * * * *